US009005419B2

(12) United States Patent
Guadagno et al.

(10) Patent No.: US 9,005,419 B2
(45) Date of Patent: Apr. 14, 2015

(54) COMPOSITION AND METHOD FOR GEL ELECTROPHORESIS WITH IN-SITU CALIBRATION

(71) Applicant: Health Diagnostic Laboratory, Inc., Richmond, VA (US)

(72) Inventors: Philip Guadagno, Mechanicsville, VA (US); Erin Summers, Glen Allen, VA (US)

(73) Assignee: Health Diagnostic Laboratory, Inc., Richmond, VA (US)

( * ) Notice: Subject to any disclaimer, the term of this patent is extended or adjusted under 35 U.S.C. 154(b) by 54 days.

(21) Appl. No.: 13/904,830

(22) Filed: May 29, 2013

(65) Prior Publication Data

US 2013/0319864 A1    Dec. 5, 2013

Related U.S. Application Data

(60) Provisional application No. 61/652,608, filed on May 29, 2012, provisional application No. 61/779,567, filed on Mar. 13, 2013.

(51) Int. Cl.
G01N 27/447    (2006.01)

(52) U.S. Cl.
CPC .... *G01N 27/44704* (2013.01); *G01N 27/44743* (2013.01)

(58) Field of Classification Search
USPC .................................. 204/606–621
See application file for complete search history.

(56) References Cited

U.S. PATENT DOCUMENTS

| 5,843,295 A | 12/1998 | Steiner et al. |
| 7,384,525 B2 | 6/2008 | Liu et al. |
| 2002/0166767 A1 | 11/2002 | McVey et al. |

(Continued)

FOREIGN PATENT DOCUMENTS

WO    9533989 A1    12/1995

OTHER PUBLICATIONS

H. Tsukamoto, et al. "Simplified method for the diameter sizing of serum low-density lipoprotein using polyacrylamide gradient gel electrophoresis" Clinical Chemistry and Laboratory Medicine, vol. 42, No. 9, 2004, p. 1009-1012.*

(Continued)

*Primary Examiner* — J. Christopher Ball
(74) *Attorney, Agent, or Firm* — Jeffrey N. Townes; LeClairRyan (57) ABSTRACT

The invention relates to, among other things, a method for performing electrophoresis with in-situ calibration. The method includes combining a volume of a test sample with a volume or quantity of a calibrating sample to form a final volume, where the volume of the calibrating sample includes a known concentration of a calibrator and the final volume includes a known ratio of test sample to calibrating sample. The method also includes depositing a loading fraction in a receiving well of an electrophoretic gel, in which the loading fraction is a fraction of the final volume, and separating the loading fraction along a common separation lane of the electrophoretic gel such that components of the test sample and the calibrator are separated from one another along the common separation lane. The method also includes detecting the calibrator and separated components of the test sample within the common separation lane and measuring the level of the calibrator and separated components of the test sample based on the detecting, thereby performing electrophoresis with in-situ calibration.

22 Claims, 5 Drawing Sheets

(56) References Cited

U.S. PATENT DOCUMENTS

| | | |
|---|---|---|
| 2003/0032042 A1 | 2/2003 | Hunkapiller et al. |
| 2012/0052594 A1 | 3/2012 | Guadagno et al. |
| 2014/0243431 A1 | 8/2014 | Guadagno et al. |

OTHER PUBLICATIONS

Goux et al., "Capillary Gel Electrophoresis Analysis of Apolipoproteins A-I and A-II in Human High-Density Lipoproteins," Anal. Biochem. 218(2):320-324 (1994).

Scherer et al., "Plasma Protein Profiling: the Diagnostic Evaluation of Disorders in Plasma Protein Composition by a New Immunoelectrophoretic Method," Clin. Chim. Acta 66(3):417-433 (1976).

Stocks et al., "Analysis of High Density Lipoprotein Apolipoproteins by Capillary Zone and Capillary SDS Gel Electrophoresis," J. Lipid Res. 39(1):218-227(1998).

Xu, "Capillary Electrophoresis," Anal. Chem. 67(12):463-473 (1995).

* cited by examiner

COMPOSITION AND METHOD FOR GEL ELECTROPHORESIS WITH IN-SITU CALIBRATION

This application claims priority benefit of U.S. Provisional Patent Application No. 61/652,608, filed May 29, 2012, and U.S. Provisional Patent Application No. 61/779,567, filed Mar. 13, 2013, each of which is hereby incorporated by reference in its entirety.

FIELD OF THE INVENTION

The invention relates to the field of gel electrophoresis, and particularly in situ calibration within an electrophoretic matrix.

BACKGROUND OF THE INVENTION

Electrophoresis is a technique used to separate charged species on the basis of size, electric charge, and other physical properties. In electrophoresis, the charged species migrate through a conductive electrophoretic medium, which may be (but is not required to be) a gel, under the influence of an electric field. Activated electrodes located at either end of the electrophoretic medium provide the driving force for the migration. The properties of the molecules, including their charge and mass, determine how rapidly the electric field causes them to migrate through the electrophoretic medium.

Many important biological molecules, such as amino acids, peptides, proteins, nucleotides, and nucleic acids, possess ionizable groups. Because of these ionizable groups, at any given pH, many important biological molecules exist in solution as electrically charged species. The electrically charged species enable doctors and scientists to separate nucleic acids and proteins using electrophoresis.

Separation of molecules, biological or otherwise, using electrophoresis depends on various forces, including charge and mass. When a biological sample, such as a protein or DNA, is mixed in a buffer solution and applied to an electrophoretic medium, these two forces act together. Separation using electrophoresis is possible because the rate of molecular migration through the electric field depends on the strength of the field, the charge, size, and shape of the molecules, and the ionic strength and temperature of the buffer through which the molecules are moving. During electrophoresis, the applied electrical field causes the molecules to move through the pores of the electrophoretic medium based on the molecular charge. The electrical potential at one electrode repels the molecules while the potential at the other electrode simultaneously attracts the molecules. The frictional force of the electrophoretic medium also aids in separating the molecules by size. Typically, after the applied electrical field has been removed, the molecules may be stained. After staining, the separated macromolecules can be seen in a series of bands spread from one end of the electrophoretic medium to the other. If these bands are sufficiently distinct, the molecules in these zones can be examined and studied separately by fixing macromolecules and washing the electrophoretic medium to remove the buffer solution.

Casting of electrophoresis gels, e.g. those of polyacrylamide or agarose, is commonly done by creating a series of sample wells in the gel surface. Liquid mixtures to be analyzed are loaded into the well, typically using a pipette, syringe needle, electrophoretic comb, or similar sample delivering instrument. However, intra-sample band resolutions are only as good as the width of the sample applied, and because small sample volumes are subject to surface tension (establishing micelle diameters in excess of the resolution desired for loading sample in a particular well) such band resolutions are poor and variable. In addition, microvolumes are often applied in a 2-D-like approach which prevents volumetric applications. Further, sample kinetics within the gel are limited relative to free solution chemistries; compromised degrees of freedom negatively affect uniform product or adduct development, except in localized areas that are often only a few sample lanes in dimension. For these reasons, sample reproducibility at the 1 uL level is often too imprecise to be clinically/analytically acceptable.

In addition, there is great difficulty in determining the concentration of fractions of a test sample separated within an electrophoretic matrix without use of an external method. Attempts to incorporate such a reference internal standard within an electrophoretic assay have been unsuccessful. Traditional attempts at polyvalent antiseras and multiple proteins failed due to variable avidity and dye binding characteristics. Qualitative markers of identity and positional references are available, but none use an internal reference standard that would allow concentrations for electrophoretically separated fractions to be absolutely quantitated independent of external methods.

There is no predicate technology in this area. Electrophoresis has been and remains the analytic derivative of "total" chemistries, where all components of a sample undergo the same processing. Components are not removed by precipitation, capture, or other method; they are separated on the same substrate and can be recombined by reversing the process. This fact has limited the capacity of electrophoresis to generate absolute quantity values. Conventional electrophoresis measures relative concentrations, i.e., it calculates percentage fractions as the area under curves from detected bands that have been translated into signals to produce electropherograms. In particular, after electrophoresis, a stained gel is passed through the optical system of a densitometer to create an electrophoregram, a visual diagram or graph of the separated bands. A densitometer is a special spectrophotometer that measures light transmitted through a solid sample such as a cleared or transparent but stained gel. Using the optical density measurements, the densitometer represents the bands as peaks. These peaks compose the graph or electrophoregram and are printed on a recorder chart or computer display. Absorbance and/or fluorescence can be measured with densitometry. An integrator or microprocessor evaluates the area under each peak and reports each as a percent of the total sample. For example, if the electrophoresis is being used for separation of serum proteins, the concentration of each band is derived from this percent and the total protein concentration; if the electrophoresis is being used for separation of enzymes, the enzyme activity of each band is derived from this percent and the total enzyme activity.

Thus, conventional electrophoresis can only assign relative percentage values for all bands detected within a sample. For example, if multiple bands are developed for cholesterol, relative percentages are provided by a densitometer and an externally-provided total cholesterol value is proportionately distributed amongst the fractions to determine absolute concentrations. For example, two bands are detected by densitometer—the first is 25% and the second 75% of the total signal detected. Given a total analyte concentration of 200 mg/mL, the first band is 50 mg/mL, (0.25×200 mg/mL), the second is 150 mg/mL, (0.75×200 mg/mL). No method exists to provide calibrators on a gel and/or within each individual sample.

Because electrophoresed patterns are only as useful as their resolutions, and due to the problems noted above, a great need exists for a method and/or system that removes the inter-sample variability and intra-sample errors associated with gel electrophoresis technology.

This invention is directed to overcoming these and other deficiencies in the art.

SUMMARY OF THE INVENTION

One aspect of the invention relates to a method for performing electrophoresis with in-situ calibration. The method includes combining a volume of a test sample with a volume or quantity of a calibrating sample to form a final volume, in which the volume or quantity of the calibrating sample includes a known concentration of a calibrator and the final volume includes a known ratio of test sample to calibrating sample. The method also includes depositing a loading fraction in a receiving well of an electrophoretic gel, in which the loading fraction is a fraction of the final volume and separating the loading fraction along a common separation lane of the electrophoretic gel such that components of the test sample and the calibrator are separated from one another along the common separation lane. The method also includes detecting the calibrator and separated components of test sample within the common separation lane and measuring the level of the calibrator and separated components of the test sample based on the detecting, thereby performing electrophoresis with in-situ calibration.

The invention provides significant and unexpected advantages. In a simple example, a known concentration of analyte (i.e., calibrator) to be measured is pre-tagged with an identical reporter as an unknown component of a test sample. The tagged internal standard and unknown are volumetrically combined and both calibrator and unknown sample are applied and electrophoresed simultaneously. An electropherogram displaying unknown fractions is analyzed to calculate the concentration of unknown components relative to the internal reference standard (i.e., calibrator). Thus, given the known concentration of the internally tagged calibrator, and the defined volumetric proportions of calibrator and sample, a single point calibrator scenario, known to those skilled in the art, can be used to calculate unknown analyte concentrations. The approach disclosed in this application removes inter-method concentrations variables and the need for external testing, and provides enhanced within-sample control and confidence, saving time, cost, and inter-method variance.

BRIEF DESCRIPTION OF THE DRAWINGS

FIG. 2 is a schematic illustration showing an exemplary gel electrophoresis apparatus and comb applicator. Application of the mixed samples to a gel may be carried out with an electrophoretic comb. The comb may include a one-dimensional array of teeth, each able to deliver approximately one microliter of sample to the gel in a single starting line for each electrophoretic lane corresponding to a tooth of the electrophoretic comb. As shown in FIG. 2, the gel is in contact with electrodes on each side of the applied sample. The apparatus may include a housing containing within its volume the electrophoretic apparatus shown in FIG. 2, which is loaded with buffer solution prior to carrying out gel electrophoresis.

FIG. 4A shows the use of a detection device to detect fluorescence intensity (I) from the fluorescent material (or fluorescent tag) on the components or unknown of the test sample ($I_U$) within an electrophoretic sample lane. FIG. 4B Shows the detection of the fluorescence intensity from the fluorescent material (or fluorescent tag) on the known calibrator sample ($I_C$) within the same lane as in the components of the test sample shown to be detected in FIG. 4A. The two measured intensities can be used, along with the known concentration of calibrator and known volumes, to calculate the concentration of the one or more components. As shown in FIGS. 4A and 4B, the detection device may include a computing device that includes, for example, optical detection software.

FIGS. 5A-5E show results of conducting gel electrophoresis with in-situ calibration according to one embodiment of the present invention. In particular, four serum samples containing unknown concentrations of lipoparticles were mixed with respective known concentrations of fluorescein-labeled albumin. The samples were subjected to gel electrophoresis and then contacted with fluorescein-labeled anti-apoB antibodies. An image of the resulting gel is shown in FIG. 5A, with the image corresponding to each of samples 1-4 reproduced in FIGS. 5B-5E, respectively. The gel was then scanned with a fluorimeter and the resulting peaks were plotted as shown in FIGS. 5B-5E. In FIGS. 5B-5E, LDL, VLDL, Lp(a), and the calibrator are identified visually in the image of the gel on the left and the results of quantifying the separated components according to the present invention is shown at the right.

DETAILED DESCRIPTION OF THE INVENTION

One aspect of the invention relates to a method for performing electrophoresis with in-situ calibration. The method includes combining a volume of a test sample with a volume or quantity of a calibrating sample to form a final volume, in which the volume or quantity of the calibrating sample includes a known concentration of a calibrator and the final volume includes a known ratio of test sample to calibrating sample. The method also includes depositing a loading fraction in a receiving well of an electrophoretic gel, in which the loading fraction is a fraction of the final volume and separating the loading fraction along a common separation lane of the electrophoretic gel such that components of the test sample and the calibrator are separated from one another along the common separation lane. The method also includes detecting the calibrator and separated components of test sample within the common separation lane and measuring the level of the calibrator and separated components of the test sample based on the detecting, thereby performing electrophoresis with in-situ calibration.

The test sample may be a biological sample. Suitable biological samples or biosamples include human biological matrices, urine, plasma, serum, and human lipoprotein fractions. For example, the sample may be fresh blood or stored blood or blood fractions. The sample may be a blood sample expressly obtained for the assays of this invention or a blood sample obtained for another purpose which can be sub-sampled for use in accordance with the methods described herein. For instance, the biological sample may be whole blood. Whole blood may be obtained from the subject using standard clinical procedures. The biological sample may also be plasma. Plasma may be obtained from whole blood samples by centrifugation of anti-coagulated blood. The biological sample may also be serum. The sample may be pre-treated as necessary by dilution in an appropriate buffer solution, concentrated if desired, or fractionated by any number of methods including but not limited to ultracentrifugation, fractionation by fast performance liquid chromatography (FPLC), or precipitation. Any of a number of standard aqueous buffer solutions, employing one of a variety of buffers, such as phosphate, Tris, or the like, at physiological to alkaline pH can be used.

As noted above, the method includes combining a volume of a test sample with a volume or quantity of a calibrating sample to form a final volume, in which the volume of the calibrating sample includes a known concentration of a calibrator and the final volume includes a known ratio (e.g., volumetric ratio) of test sample to calibrating sample.

As a person of ordinary skill in the art will appreciate, this method may be carried out with a volume of calibrator or with, for example, a known quantity of calibrator. Throughout the description herein, it will be understood that in referring to a volume of calibrator, a known quantity of calibrator may be substituted. For instance, a calibrator may be dried upon the walls of the sample cup or well and re-solubilized upon addition of the volume of the test sample. In particular, after drying the calibrator within the sample well, the remaining residue maintains the concentration of calibrator, e.g., a fluorescent tagged calibrator, without affecting volume. Upon addition of the sample, the tagged calibrator may be reconstituted and incorporated within the final volume of sample-calibrator "mix" without affecting lipid particle concentrations. Electrophoretic sample wells can be prepared in this fashion in advance of sample deposition for convenience and simplicity. Thus, another aspect of the present invention relates to electrophoretic gels prepared in this fashion, as well as kits including such gels and instructions for carrying out the methods described herein.

Combining the volume of a test sample with a volume of a calibrating sample to form a final volume may be carried out by any means suitable. The volume of the calibrating sample may be added to a volume of test sample or a volume of test sample may be added to a volume of calibrating sample, so long as the concentration of calibrator within the calibrating sample is known and the final volume includes a known ratio (e.g., volumetric ratio) of test sample to calibrating sample. In this way, calculating the concentration of the components of the test sample in the final volume is possible.

Figure 1:
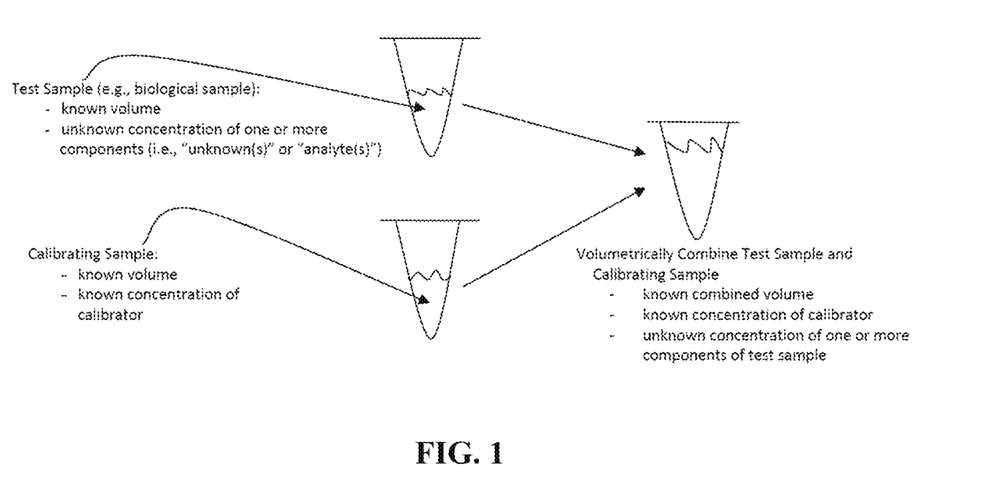
FIG. 1 is a schematic illustration showing exemplary initial volumes of a test sample (e.g., a biosample) and calibrating sample provided for carrying out electrophoresis as described herein. The biosample in this example contains one or more components (unknown(s) or analyte(s)) of interest and the calibrating sample includes a calibrator as described herein. The volume of calibrating sample includes a known concentration of the calibrator. The volume of test sample includes an unknown concentration of one or more component of interest. The volume of test sample and the volume of calibrating sample are each known. As schematically shown, the volume of test sample and the volume of calibrating sample are combined or mixed to a final known volume (i.e., volume of calibrating sample+volume of test sample).

For example, a stock internal standard (calibrator) is mixed (e.g., volumetrically) with a sample to be analyzed (see FIG. 1). Both reporter and stoichiometry of the standard and unknown sample may be characterized. Separated fractions are scanned using, for example, a densitometer. The areas under the corresponding curve of an electrophoregram are compared to the signal provided by the internal reference standard. Given the known volumetric ratio (i.e., defined linearity), single point calibration and, thus, the ability to determine concentrations of components in the test sample using an in situ calibrator is possible.

In a simple example, a known concentration of analyte (i.e., calibrator) to be measured may be pre-tagged with an identical reporter as an unknown component of a test sample. The tagged calibrator and unknown are volumetrically combined and both calibrator and unknown sample are applied and electrophoresed simultaneously. An electropherogram displaying unknown fractions is analyzed to calculate the concentration of unknown components relative to the internal reference standard (i.e., calibrator). Thus, given the known concentration of the internally tagged calibrator, and the defined volumetric proportions of calibrator and sample, a single point calibrator scenario (i.e., calibration with a single reference internal standard, which is known to those skilled in the art) can be used to calculate unknown analyte concentrations. This approach removes inter-method concentrations variables and the need for external testing (e.g., to provide total analyte concentrations), and provides enhanced within-sample control and confidence.

Accordingly, the method may also include calculating the concentration of the components of the test sample in the final volume based on the measured level of the calibrator, the measured level of the separated components of the test sample, and the known ratio (e.g., volumetric ratio) of test sample to calibrating sample.

For example, a known volume of test sample containing one or more biomolecules of interest may be contained in a test tube. A second test tube may contain a calibrating sample having a known volume and known concentration of a fluorescently-tagged calibrator, such as fluorescently-tagged albumin. The initial concentration of calibrator may be denoted $C_{Ci}$ and the initial volume or quantity of calibrator may be denoted $V_{Ci}$. The initial concentration of unknown (in this example, the one or more biomolecules of interest) may be denoted $C_{Ui}$ and the initial volume of unknown may be denoted $V_{Ui}$.

The initial volumes (or quantity) of the calibrating sample and test sample (containing the one or more biomolecules of interest) may be combined to generate a final volume, $V_F$, and final concentrations $C_{Cf}$ and $C_{Uf}$ such that:

$$V_F = V_{Ci} + V_{Ui}$$

$$C_{Cf} = C_{Ci} \cdot \frac{V_{Ci}}{V_F}$$

$$C_{Uf} = C_{Ui} \cdot \frac{V_{Ui}}{V_F}$$

The combined sample of known combined volume and known calibrator concentration is called the loading sample. The loading sample may be applied to an electrophoretic gel and electrophoresis may be carried out, separating the calibrator from the unknowns, and unknown components from each other.

Antisera containing a labeled antibody that recognizes or binds to the one or more unknown components of interest in the test sample may be applied to the gel and allowed to incubate for a short period of time. The gel may then be washed to remove unbound antibody and/or material in/on the gel. In this way, the unknown(s) of interest in the gel may bind with an antibody labeled with the same tag as the calibrator.

In this example, a detection system or device may be configured to detect the fluorescent tags on the antibodies and calibrator. For instance, a fluorescence detection unit may be used to excite fluorescent tags and measure the intensity of fluorescence from the tags. Fluorescent intensity from the tagged antibody on the unknown may be denoted $I_U$ and the fluorescent intensity from the calibrator tag may be denoted $I_C$. The unknown and the calibrator may be labeled with the same tag, the calibrator directly and the unknown linked by a bound antibody, so the fluorescence intensity from each will be different only by nature of the different numbers of particles. Particle number is directly related to concentration, which is known for the calibrator. The initial concentration of the unknown $C_{Uf}$ can thus be calculated according to the following relationship:

$$C_{Ui} = C_{Cf} \frac{V_{Ui} * I_U}{V_F * I_C}.$$

As noted above, the method includes depositing a loading fraction in a receiving well of an electrophoretic gel, in which the loading fraction is a fraction of the final volume, and separating the loading fraction along a common separation lane of the electrophoretic gel such that components of the test sample and the calibrator are separated from one another along the common separation lane.

The gel electrophoresis may be one-dimensional or two-dimensional. Isoelectric focusing may also be performed.

Electrophoretic gel substrates suitable for use with the invention are known to those of skill in the art. For instance, suitable gel substrates include, but are not limited to, agarose or polyacrylamide. SDS-PAGE (polyacrylamide) gels separate proteins based on their size because the SDS coats the proteins with a negative charge. Separation of proteins on the agarose gel is by charge.

Electrophoretic gels of varying sizes may contain various numbers of lanes (e.g., one, two, three, four, five, six, seven, eight, nine, ten, etc.). The biological sample from a single individual or subject may be probed to identify multiple components and/or serum from multiple individuals may be tested. The protocols for conducting electrophoresis on different sizes of gels will be similar except that modifications may be made to optimize separation on that size of gel.

Figure 2:
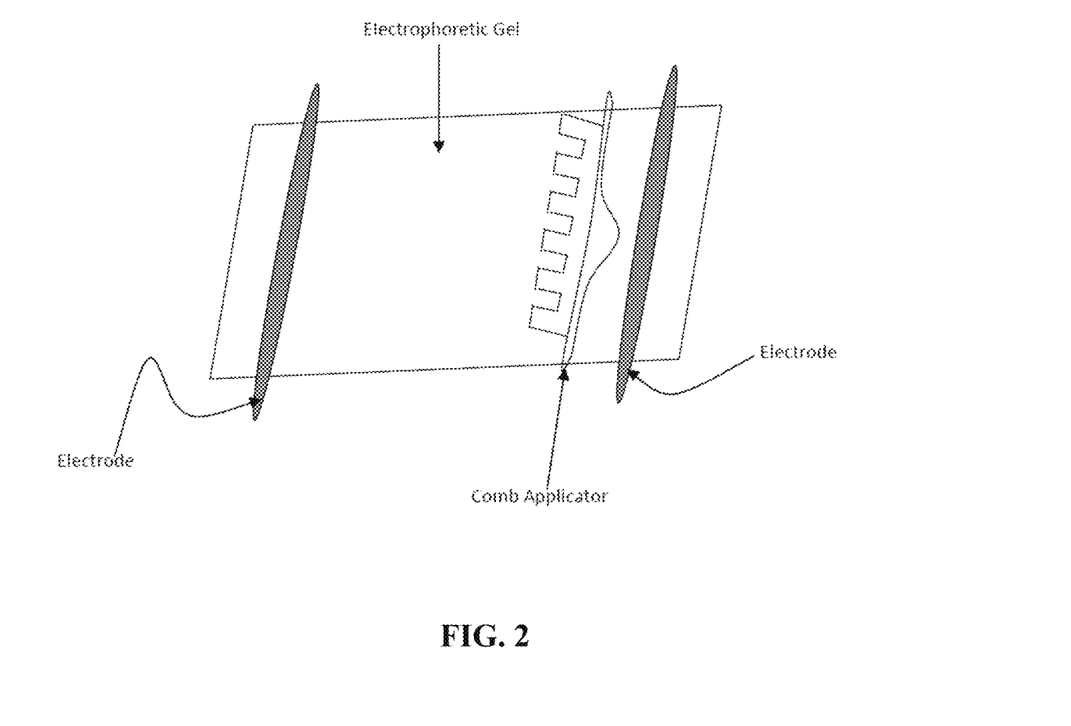

As noted above, the method may also include depositing a loading fraction onto an electrophoretic gel. The method may include depositing a loading fraction in a receiving well of an electrophoretic gel. The method may also include depositing a loading fraction onto an electrophoretic gel without a receiving well. Depositing may be carried out with an electrophoretic comb, a pipette (e.g., a micropipette), or the like. An electrophoretic comb can be particularly useful to make the deposit because the teeth of the comb can deposit a thin line of sample on the gel substrate, reducing sample diffusion. In a gel system that lacks sample reservoirs in the gel, using a pipette to deposit a sample will result in a circle of sample that diffuses in two dimensions. A diffuse sample will result in a loss of resolution in the final gel after electrophoresis because sample molecules start at all points in a circle. By depositing a sample with the one-dimensional comb teeth (see FIG. 2), diffusion is reduced and the sample molecules start from a single line; superior resolution results and shorter lanes/more sample per gel are possible.

As noted above, the method includes detecting the calibrator and separated components of test sample within the common separation lane and measuring the level of the calibrator and separated components of the test sample based on the detecting.

Figure 3:
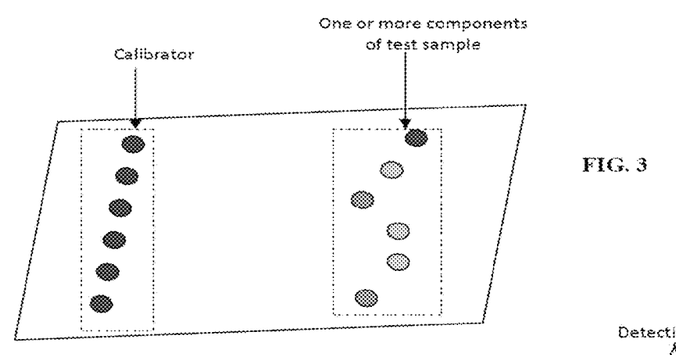
FIG. 3 is a schematic illustration showing an exemplary electrophoretic gel after gel electrophoresis has been carried out, separating the one or more components of the test sample and the calibrator. As shown in this exemplary embodiment, the calibrator and one or more components of the test sample in each lane have been separated by gel electrophoresis and are shown labeled with fluorescent material.
Figure 4A:
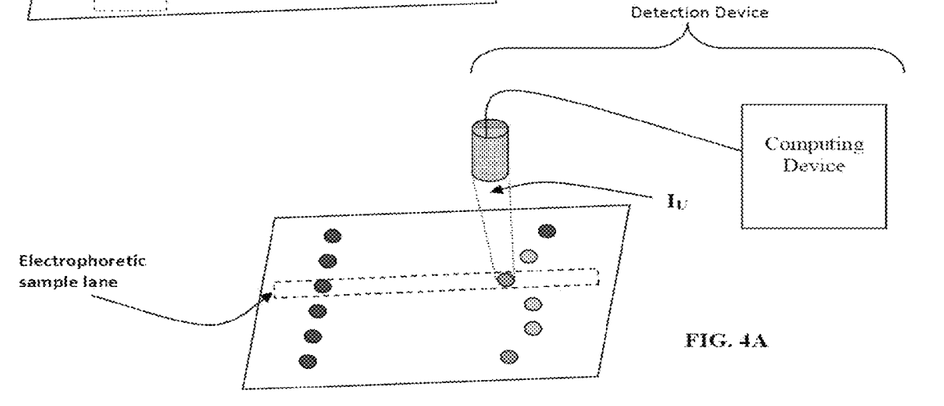
FIGS. 4A-4B are schematic illustrations showing detection of fluorescence intensity on an exemplary electrophoretic gel after gel electrophoresis has been carried out.
Figure 4B:
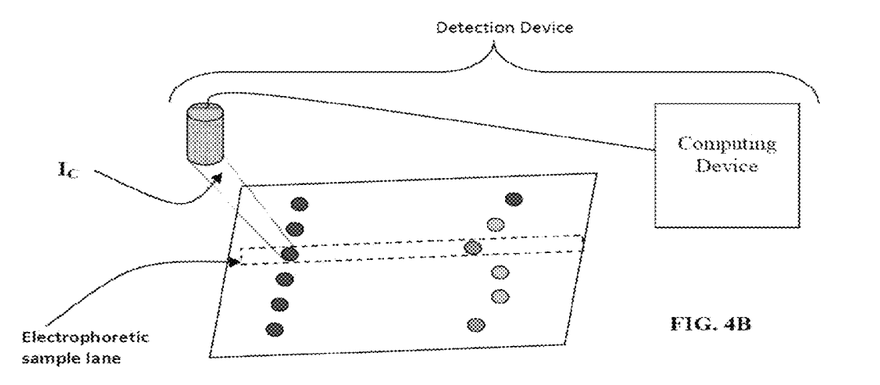

Schematic illustrations of examples of separated calibrator and components of test sample, as well as detection of separated calibrator and components of test sample are shown in FIGS. 3, 4A, and 4B.

Suitable methods of detecting include use of, for example, one or more antibodies that bind the analyte to be measured (i.e., the antibody target), or a portion thereof (e.g., the calibrator or the separated components of test sample, or portions thereof). The antibody may be bound to a signal producing molecule capable of producing or causing production of a detectable signal, thereby allowing detection of the antibody bound to the antibody target. The antibody bound to antibody target may also be detected and measured by use of a secondary antibody recognizing the primary antibody, in which the secondary antibody is bound to a signal producing molecule capable of producing or causing production of a detectable signal, thereby allowing detection of the antibody bound to the antibody target.

As noted above, in some embodiments, the one or more components of the test sample and/or the calibrator may be fixed in the electrophoretic gel, for example, by an immuno-fixation technique. This technique involves contacting the calibrator and one or more components separated by gel electrophoresis with antisera. The antisera may include a first antibody or fragment thereof, such that the first antibody or fragment thereof binds the calibrator. The antisera may also include a second antibody or fragment thereof, such that the second antibody or fragment thereof binds the one or more separated component(s). The technique may also involve washing the electrophoretic gel to remove unbound materials in the gel.

As used herein, the term "antibody" is meant to include intact immunoglobulins derived from natural sources or from recombinant sources, as well as immunoreactive portions (i.e. antigen binding portions) of intact immunoglobulins. The antibodies of the invention may exist in a variety of forms including, for example, polyclonal antibodies, monoclonal antibodies, intracellular antibodies, antibody fragments (e.g. Fv, Fab and F(ab)2), as well as single chain antibodies (scFv), chimeric antibodies and humanized antibodies (Ed Harlow and David Lane, USING ANTIBODIES: A LABORATORY MANUAL (Cold Spring Harbor Laboratory Press, 1999); Houston et al., "Protein Engineering of Antibody Binding Sites: Recovery of Specific Activity in an Anti-Digoxin Single-Chain Fv Analogue Produced in *Escherichia coli,*" *Proc Natl Acad Sci USA* 85:5879-5883 (1988); Bird et al, "Single-Chain Antigen-Binding Proteins," *Science* 242:423-426 (1988), which are hereby incorporated by reference in their entirety).

Methods for monoclonal antibody production may be carried out using techniques well-known in the art (MONOCLONAL ANTIBODIES—PRODUCTION, ENGINEERING AND CLINICAL APPLICATIONS (Mary A. Ritter and Heather M. Ladyman eds., 1995), which is hereby incorporated by reference in its entirety). Procedures for raising polyclonal antibodies are also well known (Ed Harlow and David Lane, USING ANTIBODIES: A LABORATORY MANUAL (Cold Spring Harbor Laboratory Press, 1988), which is hereby incorporated by reference in its entirety).

In addition to whole antibodies, the invention encompasses binding portions of such antibodies. Such binding portions include the monovalent Fab fragments, Fv fragments (e.g., single-chain antibody, scFv), single variable $V_H$ and $V_L$ domains, and the bivalent F(ab')$_2$ fragments, Bis-scFv, diabodies, triabodies, minibodies, etc. These antibody fragments can be made by conventional procedures, such as proteolytic fragmentation procedures, as described in James Goding, MONOCLONAL ANTIBODIES: PRINCIPLES AND PRACTICE 98-118 (Academic Press, 1983) and Ed Harlow and David Lane, ANTIBODIES: A LABORATORY MANUAL (Cold Spring Harbor Laboratory, 1988), which are hereby incorporated by reference in their entirety, or other methods known in the art.

Suitable calibrators include substances that may be separated by gel electrophoresis from the components of a test sample and detected. The calibrator and/or components of test sample may also each be directly bound to or labeled with a signal producing molecule capable of producing or causing production of a detectable signal. The signal producing molecules bound directly or indirectly to each of the calibrator and the components of the test sample may be distinguishable from each other. Further, the signal producing molecules may be bound directly or indirectly to each of the calibrator and the components of the test sample in any combination. For example, the calibrator may be directly bound to a signal producing molecule (e.g., pre-tagged with a fluorescent material) and the components of the test sample bound indirectly to a signal producing molecule. Alternatively, two or more components of the test sample may each be bound to a signal producing molecule directly or indirectly.

The calibrator may be a protein or polypeptide. For instance, the calibrator may be albumin. The calibrator may also be a compound that produces or is capable of producing a detectable signal. For example, the calibrator may be a fluorescent substance, a luminescent substance, a bioluminescent substance, or any other suitable signal producing molecule described herein.

The calibrator is distinguishable from the components of the test sample in the eletrophoretic gel. For instance, the calibrator may be or be bound to a signal producing molecule that is distinguishable from that bound to the test sample. The calibrator may also migrate on an eletrophoretic gel during gel electrophoresis at a faster rate than components of the test sample, or the calibrator may migrate on an eletrophoretic gel during gel electrophoresis at a slower rate than components of the test sample.

Suitable signal producing molecules that are capable of producing or causing production of a detectable signal will be known to those of skill in the art. The detectable signal includes any signal suitable for detection and/or measurement by radiometric, colorimetric, fluorometric, size-separation, or precipitation means, or other means known in the art.

Examples of signal producing molecules that are capable of producing or causing production of a detectable signal include various enzymes, prosthetic groups, fluorescent materials, luminescent materials, bioluminescent materials, radioactive materials, positron emitting metals, and nonradioactive paramagnetic metal ions. The signal producing molecules may be coupled or conjugated either directly to the antibody or indirectly, through an intermediate (such as, for example, a linker known in the art) using techniques known in the art. See, for example, U.S. Pat. No. 4,741,900 for metal ions which can be conjugated to antibodies for use as diagnostics according to the invention. Further examples include, but are not limited to, various enzymes. Examples of enzymes include, but are not limited to, horseradish peroxidase, alkaline phosphatase, beta-galactosidase, or acetylcholinesterase; prosthetic group complexes such as, but not limited to, streptavidin/biotin and avidin/biotin. Examples of fluorescent materials include, but are not limited to, umbelliferone, fluorescein, fluorescein isothiocyanate, rhodamine, dichlorotriazinylamine fluorescein, dansyl chloride or phycoerythrin. Examples of luminescent material include, but are not limited to, luminol. Examples of bioluminescent materials include, but not limited to, luciferase, luciferin, and aequorin. Examples of radioactive material include, but are not limited to, bismuth (213Bi), carbon (14C), chromium (51Cr), (153Gd, 159Gd) 5 gallium (68Ga, 67Ga), germanium (68Ge), holmium (166Ho), indium (115In, 113In, 112In, 111In), iodine (131I, 125I, 123I, 121I), lanthanum (140La), lutetium (177Lu), manganese (54Mn), molybdenum (99Mo), palladium (103Pd), phosphorous (32P), praseodymium (142Pr), promethium (149Pm), rhenium (186Re, 188Re), rhodium (105Rh), ruthemium (97Ru), samarium (153Sm), scandium (47Sc), selenium (75Se), strontium (85Sr), sulfur (35S), technetium (99Tc), thallium (201Ti), tin (113Sn, 117Sn), tritium (3H), xenon (133Xe), ytterbium (169Yb, 175Yb), yttrium (90Y), zinc (65Zn). Further examples include positron emitting metals using various positron emission tomographies, and nonradioactive paramagnetic metal ions.

The method may also include contacting the separated components of the test sample and/or the calibrator with a reagent capable of interacting with the signal producing molecule, in which the signal producing molecule produces the detectable signal upon contact with the reagent and in which the detecting includes detecting the detectable signal. For example, light is emitted when luciferase acts on the appropriate luciferin substrate. A secondary antibody that is coupled to a detectable signal or moiety, such as for example, an enzyme (e.g., luciferase), fluorophore, or chromophore may also be used.

The signal producing molecules used to detect the components of the test sample and the calibrator may be distinguishable from one another. The components of the test sample and the calibrator may be bound to signal producing molecules that are distinguishable from one another. This permits cocktailing of, for example, at least two signal producing molecules either directly or indirectly bound to the components of the test sample and the calibrator. This also permits cocktailing of two or more signal producing molecules either directly or indirectly bound to the calibrator and two or more a different components of test sample (e.g., lipoprotein particles or a portions thereof) each producing or capable of producing a different or distinguishable detectable signal. This permits probing of multiple antigens or analytes in a single electrophoretic lane. An example of such cocktailing is described in U.S. Provisional Patent Application No. 61/770,406, filed on Feb. 28, 2013, and titled "Fluorescent In-Situ Detection of Lipid Particle Apolipoproteins within Primary Electrophoretic Matrix," which is hereby incorporated by reference in its entirety.

For example, as noted above, the signal producing molecules may include fluorescent materials. Fluorescence tagging and the detection of natural fluorescence in molecules is a method of analytical chemistry and biology that is well known in the art. The instruments used to detect fluorescence may include the following components. A light source with a broad optical bandwidth such as a light bulb or a laser is used as the source of the stimulating light. An optical filter is used to select the light at the desired stimulation wavelength and beam it onto the sample. Optical filters are available at essentially any wavelength and are typically constructed by the deposition of layers of thin film at a fraction of the wavelength of the desired transmission wavelength. The light that exits the optical filter is then applied to the sample to stimulate the fluorescent molecule.

The molecule then emits light at its characteristic fluorescent wavelength. This light is collected by a suitable lens and is then passed through a second optical filter centered at the characteristic wavelength before being brought to a detection device such as a photomultiplier tube, a photoconductive cell, or a semiconductor optical detector. Therefore, only light at the desired characteristic wavelength is detected to determine the presence of the fluorescent molecule. Accordingly, the components of the test sample and the calibrator may be bound directly or indirectly to fluorescent molecules that emit light at different, distinguishable fluorescent wavelengths.

Fluorescent tags may be multiplexed in a single area such that they are optically distinct. For example, 5 different fluorescent tags, red, green, blue, yellow, and orange may be applied to the same limited area and be independently detected and distinguished by optical detection software. For example, the Life Technologies Alexa Fluor product line includes at least 19 distinct dyes that may be combined for tagging distinct antibodies to label and identify individual antigens.

The components of the test sample may include at least two different components, at least three different components, at least four different components, at least five different components, at least six different components, at least seven different components, at least eight different components, and so on. Accordingly, each of the different components of the test sample may be bound directly or indirectly to signal producing molecules that are distinguishable from one another and from the signal producing molecule bound directly or indirectly to the calibrator.

An optical system can quantitate the fluorescent signals and automatically normalize the signal value to generate relative densities or particle numbers. For example, by normalizing the extinction/emission coefficients or quantum relativity of each dye, relative values for concentration or number (e.g., lipoprotein particle number) can be determined.

The system and methods may also include a device or use of a device for detecting the detectable signal, in which the detecting indicates the level of the specific component of the test sample or calibrator. The device may also quantitate the level of specific components (e.g., of specific Apolipoproteins and/or lipoprotein particles) of the test sample and/or calibrator based on the detection of the signal producing molecule.

The one or more components of the test sample may include lipoprotein particles or portions thereof and in which the detecting includes detecting the lipoprotein particles or portions thereof.

The lipoprotein particles or portions thereof may be selected from the group consisting of Apolipoprotein A, Apolipoprotein B, Apolipoprotein C, Apolipoprotein D, Apolipoprotein E, Apolipoprotein H, lipoprotein (a), high density lipoprotein, intermediate density lipoprotein, low density lipoprotein, very low density lipoprotein, Chylomicrons, Lipoprotein X, oxidized variants and mixtures thereof.

The terms "lipoprotein particle," "lipid protein particle," "lipid particle," and the like as used herein refers to a particle that contains both protein and lipid. Examples of lipoprotein particles are described in more detail below.

The term "lipoprotein particle number" as used herein refers to the number of the lipoprotein particles present in the bodily fluid.

The term "apolipoprotein" as used herein refers to a protein that combines with lipids to form a lipoprotein particle. Examples of apolipoprotein types are described in more detail below. The unique nature of the apolipoprotein is their stoichiometric relationship to lipoprotein particles, providing an estimate of the lipoprotein particle number, which is described in more detail below.

As background, fatty acids, cholesterol, monoacylglycerols, and bile acids are absorbed in the intestine. Bile acids are found in intestinal bile and aid in the digestion of fats by the formation of micelles to emulsify the fats. Bile acids are stored in the gallbladder until they are secreted into the intestine after eating. Intestinal epithelial cells synthesize triacylglycerols. A portion of the cholesterol is esterified to form cholesterol esters. Intestinal cells form chylomicrons from triacylglycerols, cholesterol esters, phospholipids, free cholesterol, and apolipoproteins.

Specific lipoprotein particles or portions thereof that may be detected according to the invention include, but are not limited to, Apolipoprotein A, Apolipoprotein B, Apolipoprotein C, Apolipoprotein D, Apolipoprotein E, Apolipoprotein H, lipoprotein (a), high density lipoprotein, intermediate density lipoprotein, low density lipoprotein, very low density lipoprotein, Chylomicrons, Lipoprotein X, oxidized variants or mixtures thereof.

Apolipoproteins are the protein component of lipoprotein particles. Apolipoproteins coat lipoprotein particles that include cholesterol esters and triacylglyceride. The coat of the lipoprotein particle is made up of unesterified cholesterol, phospholipids, and apolipoproteins. The unique nature of the apolipoprotein is their stoichiometric relationship to lipoprotein particles, providing an estimate of the lipoprotein particle number. These lipoprotein particles provide a way to circulate the hydrophobic components throughout the bloodstream. Different lipoprotein particles include chylomicron-P, VLDL-P, IDL-P, LDL-P, Lp(a)-P and HDL-P. Lipoprotein particles vary in size, shape, density, apolipoprotein composition, and lipid composition. There is heterogeneity within each class with each class sharing similar physical characteristics. By varying conditions, it is possible to visualize different particles within a class. There is clinical merit in doing so because, for example, one class may be artherogenic and one class may be artheroprotective.

The apolipoprotein A (Apo A) family constitute the major proteins found in HDL-P and triglyceride-rich lipoprotein particles. Apo A, as part of HDL, is involved in the removal of free cholesterol from extrahepatic tissues and also plays a role in the activation of lecithin acyltransferase. Apolipoprotein A activates the enzymes driving cholesterol transfer from the tissues into HDL and is also involved in HDL recognition and receptors binding in the liver.

There are multiple forms of apolipoprotein A. The most common forms are Apo A-I and Apo A-II. Apolipoprotein A (A-I, A-II, and A-IV) are found in chylomicrons and HDL. Apo A-I is the major apolipoprotein A attached to HDL. Apo A-I is responsible for activating lecithin-cholesterol acyltransferase and Apo A-II modulates that activation. Lecithin-cholesterol acyltransferase converts free cholesterol into a cholesterol ester. Apo A-IV secretions increase when fat is absorbed in the intestines. Apo A-IV may also function in activation of lecithin-cholesterol acyltransferase.

Apo A-I is found in greater proportion than Apo A-II (about 3 to 1). Lower levels of Apo A commonly correlate with the presence of cardiovascular disease (CVD) and peripheral vascular disease. Apo A-I may be a better predictor of atherogenic risk than HDL-cholesterol (HDL-C). Certain genetic disorders cause Apo A-I deficiencies and associated low levels of HDL particles. These patients also tend to have hyperlipidemia with elevated LDL particles. This contributes to accelerated rates of atherosclerosis. Apo A levels may be extremely low in alpha lipoproteinemia (also known as familial high density lipoproteinemia deficiency).

The role of HDL and its major apolipoprotein Apo A-I in cholesterol efflux from macrophages has been studied extensively. While HDL competes for Apo A-I binding, Apo A-I is not a competitor for HDL binding. This observation suggests that HDL and Apo A-I are binding to macrophages at least in part by distinct receptors. For example, pre-β-HDL and lipid-free Apo A-I are poor ligands for the scavenger receptor (SR-BI), explaining the lack of competition of HDL binding by Apo A-I. Conversely, it has been shown that Apo A-I can dissociate from HDL, so that lipid-free Apo A-I could be available for the competition of the Apo A-I binding site by HDL. Lorenzi et al., "Apolipoprotein A-I but not high-density lipoproteins are internalised by RAW macrophages: roles of ATP-binding cassette transporter A1 and scavenger receptor." BIJ Mol Med. 86:171-183 (2008), which is hereby incorporated by reference in its entirety. Apo A-II, another component of HDL, has been shown to be pro-atherogenic in animal models. Meyers et al., "Pharmacologic elevation of high-density lipoproteins: recent insights on mechanism of action and atherosclerosis protection." Curr Opin Cardiol. 19(4): 366-373 (2004), which is hereby incorporated by reference in its entirety.

Apolipoprotein B (Apo B-100 and Apo B-48) is the protein component of LDL. One molecule of Apo B is present in the phospholipid layer of each LDL. Over 90% of the LDL particle is composed of Apo B. Apo B functions to solubilize cholesterol within the LDL complex, which in turn increases the transport capacity of LDL for subsequent deposit of LDL cholesterol on the arterial wall. The deposit contributes to cardiovascular disease. Apo B is also a protein component of chylomicrons, VLDL, IDL, and Lp(a). Apo B is a large amphipathic helical glycoprotein with 2 isoforms: Apo B-100 (synthesized in the hepatocytes) and Apo B-48 (the structural protein of chylomicrons). Chylomicrons contain Apo B-48 while other lipoprotein particles that contain Apo B contain Apo B-100.

Apo B modulates the activity of enzymes that act on lipoprotein particles, maintains the structural integrity of the lipoprotein particle complex, and facilitates the uptake of lipoprotein particles by acting as ligands for specific cell-surface receptors. Enzymes that act on lipoprotein particles include but are not limited to lipoprotein lipase, lecithin-cholesterol acyltransferease, hepatic-triglyceride lipase, and cholesterol ester transfer protein. Elevated levels of Apo B are found in hyperlipoproteinemia. Apo B-100 is absent in forms of abetalipoproteinemia. High levels of Apo B-100 may be present in hyperlipoproteinemia, acute angina, and myocardial infarction. Apo B-48 stays in the intestine in chylomicron retention disease.

It is well established that increased plasma concentration of Apo B-containing lipoprotein particles is associated with an increased risk of developing atherosclerotic disease. Case-control studies have found plasma Apo B concentrations to be more discriminating than other plasma lipids and lipoprotein particles in identifying patients with coronary heart disease (CHD). See De Backer et al., "European Guidelines on Cardiovascular Disease Prevention in Clinical Practice. Third Joint Task Force of European and other Societies on Cardiovascular Disease Prevention in Clinical Practice," Eur Heart J 24:1601-1610 (2003); Walldius & Jungner, "Apolipoprotein B and Apolipoprotein A-I: Risk Indicators of Coronary Heart Disease and Targets for Lipid-modifying Therapy," J Intern Med 255(2): 188-205 (2004); Walldius, et al., "The apoB/apoA-I ratio: A Strong, New Risk Factor for Cardiovascular Disease and a Target for Lipid-Lowering Therapy—A Review of the Evidence," J Intern Med. 259(5): 493-519 (2006); Yusuf et al., "Effect of Potentially Modifiable Risk Factors Associated with Myocardial Infarction in 52 Countries (the INTERHEART Study): Case-control Study," Lancet 364: 937-52 (2004), which are hereby incorporated by reference in their entirety). The utility of Apo B in determining CHD risk has been confirmed by prospective studies, although the extent to which Apo B concentrations were better than serum lipids in predicting risk was variable. Apo B is a component of all atherogenic or potentially atherogenic particles, including very low density lipoprotein particles (VLDL-P), intermediate density lipoprotein particles (IDL-P), low density lipoprotein particles (LDL-P), and lipoprotein(a) particles (Lp(a)-P), and each particle contains one molecule of Apo B. Therefore, Apo B provides a direct measure of the number of atherogenic lipoprotein particles in the circulation. Total Apo B is not homogeneous. Total Apo B will be influenced by its presence of Apo B in the various particles above. Measuring total Apo B alone without separating the particles does not indicate with which particle it is associated.

There is now a clear consensus that Apo B is more strongly predictive of cardiovascular disease (CVD) than low density lipoprotein cholesterol (LDL-C) and a recent consensus conference report from the American Diabetes Association (ADA) and the American College of Cardiology (ACC) recognizes the importance of measurement of Apo B (see Kannel et al., "Cholesterol in the Prediction of Atherosclerotic Disease," Ann Intern Med 90:85-91 (1979) and Jeyarajah et al., "Lipoprotein Particle Analysis by Nuclear Magnetic Resonance Spectroscopy," Clin Lab Med 26: 847-70 (2006), which are hereby incorporated by reference in their entirety). An elevated level of Apo B and LDL-P signifies that an individual has increased risk for cardiovascular disease. An elevated level of Apo B and Lp(a)-P signifies that an individual has increased risk for cardiovascular disease.

Further, the Apo B/Apo A-I ratio has been shown to be strongly related to risk of myocardial infarction (MI), stroke and other CV manifestations as shown in the Apolipoprotein-related mortality risk (AMORIS) (See Walldius & Jungner, "Apolipoprotein B and Apolipoprotein A-I: Risk Indicators of Coronary Heart Disease and Targets for Lipid-modifying Therapy," J Intern Med 255(2): 188-205 (2004); Walldius, et al., "The apoB/apoA-I ratio: A Strong, New Risk Factor for Cardiovascular Disease and a Target for Lipid-Lowering Therapy—A Review of the Evidence," J Intern Med. 259(5): 493-519 (2006); Walldius et al., "Stroke Mortality and the Apo B/Apo A-I Ratio: Results of the AMORIS Prospective Study." J Intern Med. 259: 259-66 (2006), which are hereby incorporated by reference in their entirety) and INTERHEART (Yusuf et al., "Effect of Potentially Modifiable Risk Factors Associated with Myocardial Infarction in 52 Countries (the INTERHEART Study): Case-control Study," Lancet 364: 937-52 (2004) and Yusuf et al., "Obesity and the risk of myocardial infarction in 27,000 participants from 52 countries: a case-control study," Lancet 366: 1640-9 (2005), which are hereby incorporated by reference in their entirety) studies.

Apolipoprotein C (Apo C-I, C-II, C-III) is a component of chylomicron particles, VLDL particles, IDL particles, and HDL particles. Apo C-II is an activator of lipoprotein lipase and a deficiency results in an accumulation of chylomicrons and triacylglycerols. High levels of Apo C-II are indicators of angina and myocardial infarction. Apolipoprotein C-II (Apo C-II) is a specific type of protein found in large particles absorbed from the gastrointestinal tract. It is also found in very low density lipoprotein particles (VLDL-P) which is made up of mostly cholesterol. Apo C-II is an apolipoprotein responsible for the activation of lipoprotein lipase (LPL) in capillaries and thus begins the catabolism of the chylomicron particles and VLDL-P. It is also found in HDL-P. Deficits of this Apo C-II present with grave hypertriglyceridemia and hyperchylomicronemia during fasting.

Apo C-II measurements can help to determine the specific type or cause of high blood lipids (hyperlipidemia). Persons with familial lipoprotein lipase deficiency may have high amounts of Apo C-II. Other disorders that may be associated with high Apo C-II levels include angina pectoris and heart attack. Low Apo C-II levels are seen in persons with a rare condition called familial Apo C-II deficiency.

Apolipoprotein C-III (Apo C-III) is found in very low density lipoprotein particles (VLDL-P). Apo C-III inhibits lipoprotein lipase and hepatic lipase and it is thought to inhibit hepatic uptake of triglyceride-rich particles. Apo C-IV is found in at least VLDL-P and HDL-P.

The Apo A-I, Apo C-III and Apo A-IV genes are closely linked in both rat and human genomes. The A-I and A-IV genes are transcribed from the same strand, while the A-I and C-III genes are convergently transcribed. An increase in Apo C-III levels induces the development of hypertriglyceridemia.

Apolipoprotein D is a minor component of HDL. High concentrations of Apo D are correlated with various diseases such as gross cystic disease of the breast and Alzheimer's disease.

Apolipoprotein E (Apo E-2, E-3, and E-4) are found in chylomicrons and IDL. Apo E binds to a receptor on liver cells and peripheral cells. Apo E is essential for the normal catabolism of triglyceride-rich lipoprotein particle constituents. Apo E was initially recognized for its importance in lipoprotein particle metabolism and cardiovascular disease. It plays a role in the transport of lipids to the tissues, the transport of cholesterol from the organs to the liver, in lipoprotein particle metabolism by clearing VLDL and chylomicrons, and in formation of atherosclerotic lesions. The Apo E portion of the lipoprotein particles mediates the binding of Apo E lipoprotein particles to the LDL receptor. Apo E bound to HDL-P inhibits agonist induced platelet aggregation by binding to sites on the platelets. Three different alleles of the Apo E gene exist, Apo E e2, e3, and e4. Apo E e4 is associated with an increased risk of late onset Alzheimer's disease.

Apolipoprotein H functions to bind cardiolipin. Anti-cardiolipin antibodies are found in syphilis, sclerosis, and lupus and in some diseases the antibodies require Apo H to be active and inhibit serotonin release by the platelets and prevent aggregation of platelets. Apo H also inhibits serotonin release by platelets and prevents aggregation of platelets.

Lipoprotein particle profiles are different for different individuals and for the same individual at different times. Chylomicrons are produced in the intestine and transport digested fat to the tissues. Lipoprotein lipase hydrolyzes triacylgylcerol to form fatty acids. Chylomicrons are one of the largest buoyant particles. VLDL is formed from free fatty acids upon metabolism of chylomicrons in the liver. Lipoprotein lipase hydrolyzes triacylgylcerol to form fatty acids. IDL is the unhydrolyzed triacylglycerol of VLDL. IDL becomes LDL due to hepatic lipase. HDL plays a role in the transfer of cholesterol to the liver from peripheral tissues. HDL is synthesized in the liver and intestines.

LDL particles bind to LDL receptors. Upon receptor binding, LDL is removed from the blood. Cells use cholesterol within the LDL for membranes and hormone synthesis. LDL deposits LDL cholesterol on the arterial wall which contributes to cardiovascular disease. LDL causes inflammation when it builds up inside an artery wall. Macrophages are attracted to the inflammation and turn into foam cells when they take up LDL, causing further inflammation. Smaller, denser LDL contain more cholesterol ester than the larger, buoyant LDL.

The structure of the lipoprotein(a) particles (LP(a)-P) is that of an LDL-like particle with apolipoprotein A bound to apolipoprotein B by a disulfide bond. Lipoprotein(a) particles appear to play a role in coagulation and may stimulate immune cells to deposit cholesterol on arterial walls. A high lipoprotein(a)-P level indicates a higher risk for cardiovascular disease. Specifically, a high level for a slower migrating, more cathodic, Lp(a)-P band may be an indicator of higher risk for cardiovascular disease, as it may be associated with the smaller more atherogenic Lp(a)-P isoform Therefore, Lp(a)-P is useful in diagnostic and statistical risk assessment. Lp(a)-P may serve to facilitate LDL-P plaque deposition. Levels of Lp(a)-P are increased in atherogenic events.

Lp(a)-P may have a link between thrombosis and atherosclerosis, interfering with plasminogen function in the fibrinolytic cascade. Numerous studies have documented the relationship of high plasma Lp(a)-P concentrations to a variety of cardiovascular disorders, including peripheral vascular disease, cerebrovascular disease, and premature coronary disease. One large study of older Americans, in particular, demonstrated elevated levels of Lp(a)-P independently predict an increased risk of stroke, death from vascular disease, and death from all causes in men (see Fried et al., "The Cardiovascular Health Study: Design and Rationale," *Ann. Epidemiol.* 3:263-76 (1991), which is hereby incorporated by reference in its entirety).

Low-density lipoprotein cholesterol, (LDL-C), has been used for measurement for assessing cardiovascular risk. However, due to the variability of HDL-C, Apo B is a better measure of circulating LDL particle number (LDL-P) and therefore a more reliable indicator of risk than that traditional LDL-C because there is 1:1 stoichiometry of Apo B and LDL particles. The sum of total Apo B includes but is not limited to the Apo B complement of LDL-P (large buoyant particles and small dense particles), +VLDL+IDL+Lp(a)+chylomicrons. Measurement of Apo B levels and associated lipoprotein particles provides additional information on the risk of atherosclerotic heart disease beyond that of the individual measurements or the traditional LDL-C assays. Measurement of fasting plasma insulin levels and LDL particle size also provide useful information.

Oxidized variants of the above-noted lipoproteins may also be detected. Oxidized variants of lipoproteins contribute to atherogenesis, with oxidation leading to increased intracellular calcium, lowered energy production, activation of cytokines, membrane damage, all resulting in apoptosis, necrosis, and ultimately cell death. Oxidation typically begins when a reactive radical abstracts a hydrogen atom from a polyunsaturated fatty acid on the LDL particle. Lipid peroxyl and alkoxyl radicals are formed, which in turn can initiate oxidation in neighboring fatty acids, resulting in propogation of lipid peroxidation. These oxidized forms of lipoproteins are absorbed by macrophages more rapidly than the native lipoproteins and this results in macrophage cholesterol accumulation, and subsequent foam cell formation and inhibition of the motility of tissue macrophages and endothelial cells. This cascade of events results in vascular dysfunction and formation and activation of atherosclerotic lesions.

The presence of the lipoprotein particle or a portion thereof in the electrophoretic gel may then be quantified by measurement of the detectable signal or moiety. The particle number may then be calculated according to known stoichiometric relationships (e.g., 1:1 stoichiometry of Apo B and LDL particles). The particle number may be quantified by comparison with a separate analysis that characterizes the total lipid particle or class of lipid particle concentration in the sample. Such separate analysis may be ultracentrifugation, NMR, or any other analysis method that can characterize a concentration or total particle number for particles in the sample. Said sample used in lipid particle electrophoresis and lipid particle quantification may be different aliquots of the same sample.

Accordingly, another aspect of the invention relates to a method of assessing the level of specific Apolipoproteins and/or lipoprotein particles present in a biological sample by carrying out the method for performing electrophoresis with in-situ calibration, in which the components of the test sample include lipoprotein particles or portions thereof and in which the detecting includes detecting the lipoprotein particles or portions thereof.

In this way, it may be determined whether a subject is at increased risk for cardiovascular disease by assessing the level of specific Apolipoproteins and/or lipoprotein particles present in a biological sample. The method may also include the step of correlating the determined level of the Apolipoprotein and/or lipoprotein particle to a control or reference value to determine if the subject is at an increased risk for cardiovascular disease.

The assessing may include separating lipoprotein particles present in the biological sample by depositing the biological sample on an electrophoretic gel and carrying out gel electrophoresis; detecting the detectable signal produced by the signal producing molecules of the respective Apolipoproteins and/or lipoprotein particles and the calibrator on the electrophoretic gel; and determining the levels of the different Apolipoproteins and/or lipoprotein particles present in the biological sample based on the detecting. As described above, the signal producing molecules may be bound directly or indirectly (e.g., via antibody) to the Apolipoproteins and/or lipoprotein particles and the calibrator. If bound indirectly (e.g., via antibody), the assessing may also include contacting the biological sample with antibody bound to a signal producing molecule under conditions suitable to form a lipoprotein-antibody-signal producing molecule complex and/or calibrator-antibody-signal producing molecule complex and washing the gel to eliminate, or substantially eliminate, unbound antibody and detecting the detectable signal produced by the signal producing molecules of the respective Apolipoproteins and/or lipoprotein particles and the calibrator on the electrophoretic gel. As also described above, the method may also be carried out with a primary and secondary antibody, in which the secondary antibody is bound to the signal producing molecule. In this embodiment, the assessing may also include contacting the biological sample with a primary antibody under conditions suitable to form a lipoprotein-primary antibody complex and/or calibrator-primary antibody complex and washing the gel to eliminate, or substantially eliminate, unbound primary antibody; contacting the lipoprotein-primary antibody complex and/or calibrator-primary antibody with a secondary antibody bound to a signal producing molecule under conditions suitable to form a lipoprotein-primary antibody-secondary antibody-signal producing molecule complex and/or calibrator-primary antibody-secondary antibody-signal producing molecule complex and washing the gel to eliminate, or substantially eliminate, unbound secondary antibody; and detecting the detectable signal produced by the signal producing molecules of the respective Apolipoproteins and/or lipoprotein particles and the calibrator on the electrophoretic gel.

As noted above, the signal producing molecules bound directly or indirectly to each of the calibrator and the components of the test sample (e.g., one or more Apolipoproteins and/or lipoprotein particles) may be distinguishable from each other. Further, the signal producing molecules may be bound directly or indirectly to each of the calibrator and the components of the test sample (e.g., one or more Apolipoproteins and/or lipoprotein particles) in any combination. For example, the calibrator may be directly bound to a signal producing molecule (e.g., pre-tagged with a fluorescent material) and the components of the test sample bound indirectly to a signal producing molecule. Alternatively, two or more components of the test sample (e.g., one or more Apolipoproteins and/or lipoprotein particles) may each be bound to a signal producing molecule directly or indirectly.

Correlation in the context of lipid-related health risk, cardiovascular condition, and risk of cardiovascular disease, refers to a statistical correlation of the resulting lipoprotein size distribution with population mortality and risk factors, as well known in the art. Correlation in the context of monitoring cardiovascular risk (e.g., for responsiveness to a therapeutic intervention) refers to comparison of the lipoprotein size distribution at two time points (e.g., before and after a therapeutic intervention is conducted).

The correlating may include correlating the determined levels of the different Apolipoproteins and/or lipoprotein particles to a control or reference value to determine if the subject is at an increased risk for cardiovascular disease.

The correlating may also include assigning the subject to a risk category selected from the group consisting of high risk, intermediate risk, and low risk (or optimal) groups for developing or having cardiovascular disease. There are well established recommendations for cut-off values for biochemical markers (for example, and without limitation, cholesterol and lipoprotein levels) for determining risk. For instance, anti-ApoB binding/detection may be correlated to cut-off estimates for assigning a risk category based on Lp(a)-P and LDL-P. For instance, the cut-off values for assigning such risk categories may be as follows: Lp(a)-P: <75 nmol/L optimal, 76-125 nmol/L intermediate risk, >126 nmol/L high risk; LDL-P: <1000 nmol/L optimal, 1000-1299 nmol/L intermediate risk, >1300 nmol/L high risk.

The above one or more different lipoprotein particles or portions thereof may include at least Apolipoprotein B and low density lipoprotein. An elevated level of Apolipoprotein B and low density lipoprotein particles detected indicates that an individual has increased risk for cardiovascular disease. Since there is a 1:1 stoichiometry between ApoB and VLDL, an elevated ApoB is arithmetically related to VLDL-P.

The different lipoprotein particles or portions thereof may include at least Apolipoprotein B and lipoprotein (a). An elevated level of lipoprotein (a) particles and Lp(a)-Isoform type detected indicates that an individual has increased risk for cardiovascular disease.

The invention also includes selecting a therapy regimen based on the risk for cardiovascular disease determined. For instance, an individual may be determined to be at an elevated risk according to the methods described herein and a treatment regimen may then be selected based on the elevated risk.

The selected therapy regimen may include drugs or supplements. Suitable drugs or supplements include those administered for the purpose of lowering serum cholesterol, lowering LDL, IDL, and VLDL, Lp(a) and/or raising HDL, as known in the art.

Examples of suitable drugs include an anti-inflammatory agent, an antithrombotic agent, an anti-platelet agent, a fibrinolytic agent, a lipid reducing agent, a direct thrombin inhibitor, a glycoprotein IIb/IIIa receptor inhibitor, an agent that binds to cellular adhesion molecules and inhibits the ability of white blood cells to attach to such molecules, a calcium channel blocker, a beta-adrenergic receptor blocker, an angiotensin system inhibitor, or combinations thereof.

The selected therapy regimen may also involve giving recommendations on making or maintaining lifestyle choices based on the risk for cardiovascular disease determined. Lifestyle choices may involve changes in diet, changes in exercise, reducing or eliminating smoking, or a combination thereof.

A report may also be generated that includes, among other things, a description of the selected treatment regimen. In some embodiments, the results of lipoprotein analyses are reported in such a report. A report refers in the context of lipoprotein and other lipid analyses to a report provided, for example to a patient, a clinician, other health care provider, epidemiologist, and the like, which includes the results of analysis of a biological specimen, for example a plasma specimen, from an individual. Reports can be presented in printed or electronic form, or in any form convenient for analysis, review and/or archiving of the data therein, as known in the art. A report may include identifying information about the individual subject of the report, including without limitation name, address, gender, identification information (e.g., social security number, insurance numbers), and the like. A report may include biochemical characterization of the lipids in the sample, for example without limitation triglycerides, total cholesterol, LDL cholesterol, and/or HDL cholesterol, and the like. A report may further include characterization of lipoproteins, and reference ranges therefore, conducted on samples prepared by the methods provided herein. The term "reference range" and like terms refer to concentrations of components of biological samples known in the art to reflect typical normal observed ranges in a population of individuals. Exemplary characterization of lipoproteins in an analysis report may include the concentration and reference range for VLDL, IDL, Lp(a), LDL and HDL, and subclasses thereof. A report may further include lipoprotein size distribution trends.

The invention also may further include administering the selected treatment regimen to the subject. Accordingly, a further aspect of the present invention relates to a method of treating a subject having an elevated risk for cardiovascular disease determined.

The invention also relates to a method of monitoring the risk for developing cardiovascular disease. This method includes determining whether a subject is at increased risk for cardiovascular disease at a first time point and repeating the determining at one or more later time points (e.g., before and after therapeutic intervention or at progressive time points during a course of therapeutic intervention). The determined risk at each progressive time point is compared the determined risk from one or more earlier time points to evaluate whether the subject's risk for developing cardiovascular disease has increased or decreased, thereby monitoring the risk for developing cardiovascular disease. This method may involve assigning a risk category based on the determined risk for developing cardiovascular disease and comparing the risk categories assigned at progressive time points (e.g., comparing a first risk category determined at a first time point to a second risk category taken at a second time point), thereby monitoring the risk for developing cardiovascular disease.

EXAMPLES

Example 1

Gel Electrophoresis with In-Situ Calibration

Gel electrophoresis with in-situ calibration was carried out using materials and methods described above. In particular, four serum samples containing unknown concentrations of lipoparticles were mixed with respective known concentrations of fluorescein-labeled albumin, which was the calibrator.

The samples were then subjected to gel electrophoresis. In particular, 75 uL of sample was dispensed into the respective sample wells which contained a known concentration of calibrator previously dried upon the walls of the sample cup. Upon sample deposition, the calibrator was re-solubilized by the unknown sample forming a final volume with a known ratio of sample to calibrator. In this experiment, each of the four samples was loaded into a separate electrophoretic well along a single electrophoretic lane. The portion of the samples loaded into the gel were then separated along respective common separation lanes of the electrophoretic gel, such that components of the test sample and the calibrator were separated from one another by size and charge along the respective separation lanes.

Figure 5A:
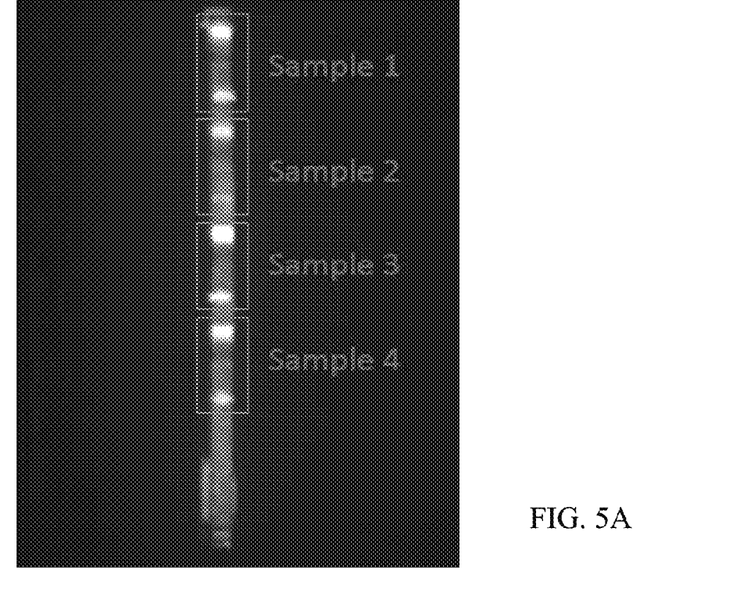
Figure 5B:
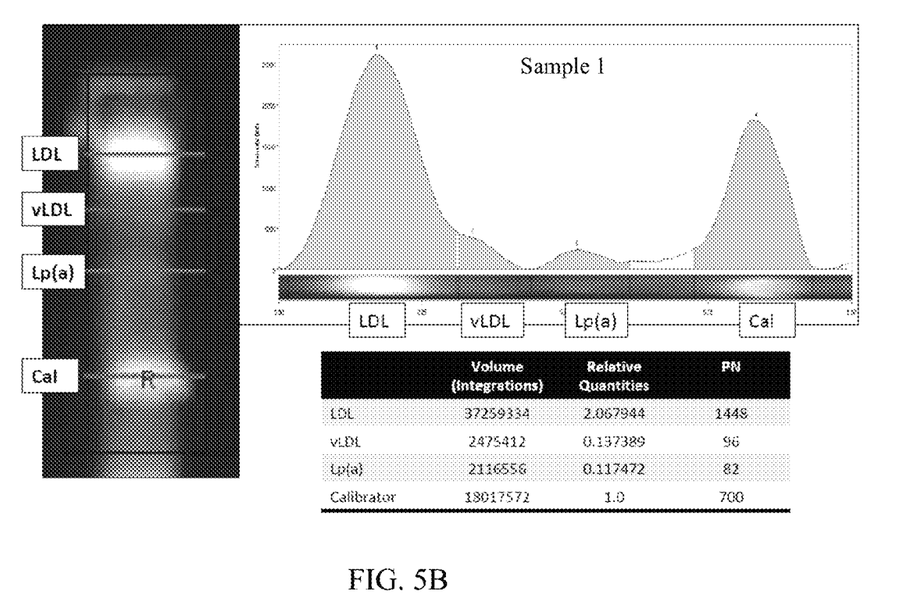
Figure 5C:
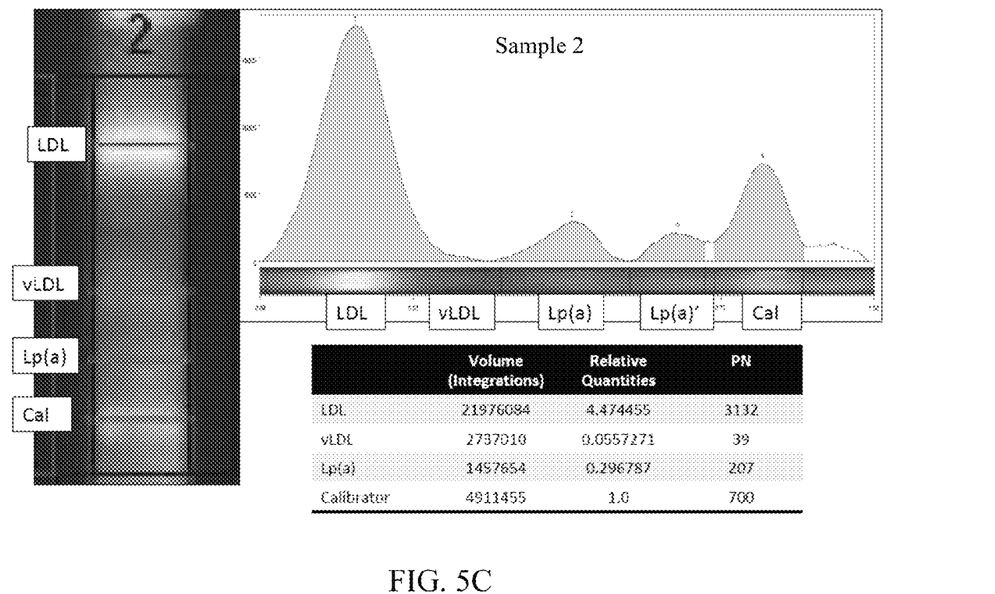
Figure 5D:
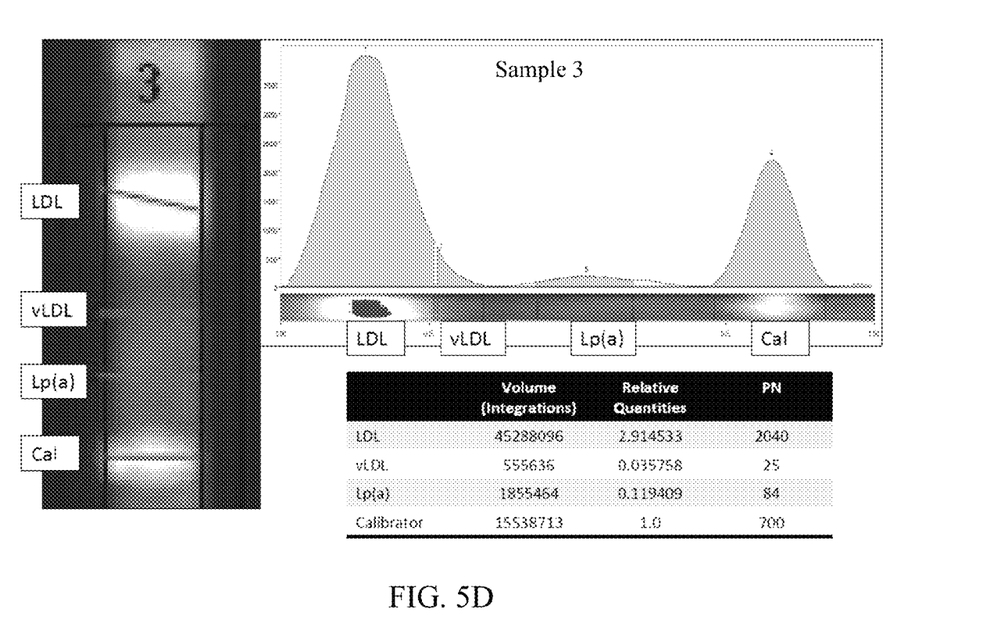
Figure 5E:
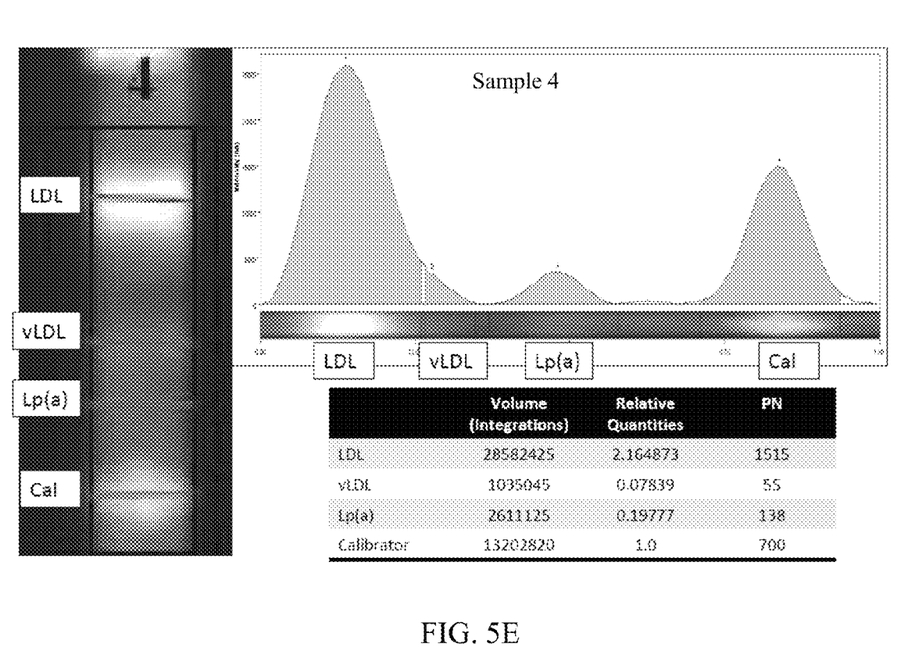

Once the separation was complete, an anti-apoB and anti-BSA-albumin "cocktail" antisera was applied to the lane in which the sample had been run. In this case, the anti-apoB antibodies were labeled with the same fluorescein as the albumin control. However, as described above, the calibrator (e.g., albumin) could have been labeled with a signal producing molecule that is different from the anti-apoB antibodies. The anti-apoB antibodies adhered to the apoB proteins on the samples' lipoprotein surfaces. LDL, VLDL, and Lp(a) include apoB. Thus, those lipoparticles bound to the anti-apoB antibodies and the BSA albumin calibrator bound to the anti-BSA-albumin antibodies were "fixed" within the gel matrix. The remaining anti-sera was removed by a typical blotting-pressing protocol with subsequent rehydration in suitable liquid to effect removal of excess unbound antisera. The process may be repeated to effect adequate removal of unbound antisera. In this circumstance, the rehydration solution was a Tris buffered saline solution, common for IFE washing protocols. An image of the resulting gel is shown in FIG. 5A.

The gel was then scanned with a fluorimeter (BioRad ChemiDoc MP imager) after drying and the resulting peaks were plotted as shown in FIGS. 5B-5E. It is noted that gels need not be dried. In FIGS. 5B-5E, LDL, VLDL, Lp(a), and the calibrator are identified visually in the image of the gel on the left and the results of quantifying the separated components according to the present invention is shown at the right for samples 1-4, respectively. Relative concentrations were generated and converted to absolute concentrations or particle number using the known concentration of calibrator, as described herein.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method for performing electrophoresis with in-situ calibration, the method comprising:
 combining a volume of a test sample with a volume of a calibrating sample to form a final volume, wherein the volume of the calibrating sample comprises a known concentration of a calibrator and the final volume comprises a known volumetric ratio of test sample to calibrating sample;

depositing a loading fraction in a receiving well of an electrophoretic gel, wherein the loading fraction is a fraction of said final volume;

separating the loading fraction along a common separation lane of the electrophoretic gel such that components of the test sample and the calibrator are separated from one another along the common separation lane, wherein the components of the test sample and the calibrator are each bound to a signal producing molecule capable of producing or causing production of a detectable signal, and wherein the components of the test sample and the calibrator are bound to signal producing molecules that are distinguishable from one another;

detecting the calibrator and separated components of test sample within the common separation lane; and measuring the level of the calibrator and separated components of the test sample based on said detecting, thereby performing electrophoresis with in-situ calibration.

2. The method according to claim 1, further comprising:
calculating the concentration of the components of the test sample in said final volume based on the measured level of the calibrator, the measured level of the separated components of the test sample, and the known volumetric ratio of test sample to calibrating sample.

3. The method according to claim 1, wherein the method further comprises:
contacting the separated components of the test sample and/or the calibrator with a reagent capable of interacting with the signal producing molecule, wherein the signal producing molecule produces the detectable signal upon contact with the reagent and wherein said detecting comprises detecting the detectable signal.

4. The method according to claim 1, wherein the components of the test sample comprise at least two different components.

5. The method according to claim 4, wherein each of the at least two components is bound to a different detectable signal, each of the detectable signals being distinguishable from one another.

6. The method according to claim 1, wherein the detectable signal is detectable by radiometric, colorimetric, luminometric, or fluorometric means.

7. The method according to claim 1, wherein said one or more components of the test sample comprises lipoprotein particles or portions thereof and wherein said detecting comprises detecting the lipoprotein particles or portions thereof.

8. The method according to claim 7, wherein the lipoprotein particles or portions thereof are selected from the group consisting of Apolipoprotein A, Apolipoprotein B, Apolipoprotein C, Apolipoprotein D, Apolipoprotein E, Apolipoprotein H, lipoprotein (a), high density lipoprotein, intermediate density lipoprotein, low density lipoprotein, very low density lipoprotein, Chylomicrons, Lipoprotein X, oxidized variants and mixtures thereof.

9. The method according to claim 1, wherein said depositing is carried out with an electrophoretic comb.

10. The method according to claim 1, wherein said calibrator is a fluorophore.

11. The method according to claim 1, wherein said calibrator comprises a protein.

12. The method according to claim 11, wherein the calibrator comprises albumin.

13. The method according to claim 12, wherein the albumin is coupled to a signal producing molecule.

14. The method according to claim 12, wherein the albumin is coupled to a fluorophore.

15. The method according to claim 1, wherein said calibrator migrates on an eletrophoretic gel during gel electrophoresis at a faster rate than components of the test sample.

16. The method according to claim 7, wherein said calibrator migrates on an eletrophoretic gel during gel electrophoresis at a faster rate than the lipoprotein particles.

17. The method according to claim 1, wherein the test sample is a biologic sample.

18. The method according to claim 1, wherein the calibrator and the separated components are fixed prior to said detecting.

19. The method according to claim 18, wherein the calibrator and separated components are fixed by an immunofixation technique, the immunofixation technique comprising:
contacting the calibrator and separated components with antisera comprising a first antibody or fragment thereof and a second antibody or fragment thereof, such that the first antibody or fragment thereof binds the calibrator and the second antibody or fragment thereof binds the separated component; and
washing the electrophoretic gel to remove unbound materials in the gel.

20. The method according to claim 1, wherein said calibrator comprises a protein or polypeptide bound to a fluorophore.

21. A method for performing electrophoresis with in-situ calibration, the method comprising:
combining a volume of a test sample with a volume of a calibrating sample to form a final volume, wherein the volume of the calibrating sample comprises a known concentration of a calibrator and the final volume comprises a known volumetric ratio of test sample to calibrating sample;
depositing a loading fraction in a receiving well of an electrophoretic gel, wherein the loading fraction is a fraction of said final volume;
separating the loading fraction along a common separation lane of the electrophoretic gel such that components of the test sample and the calibrator are separated from one another along the common separation lane, wherein the components of the test sample and the calibrator are each bound to a signal producing molecule capable of producing or causing production of a detectable signal;
contacting the separated components of the test sample and/or the calibrator with a reagent capable of interacting with the signal producing molecule, wherein the signal producing molecule produces the detectable signal upon contact with the reagent;
detecting the calibrator and separated components of test sample within the common separation lane, wherein said detecting comprises detecting the detectable signal; and
measuring the level of the calibrator and separated components of the test sample based on said detecting, thereby performing electrophoresis with in-situ calibration.

22. A method for performing electrophoresis with in-situ calibration, the method comprising:
combining a volume of a test sample with a volume of a calibrating sample to form a final volume, wherein the volume of the calibrating sample comprises a known concentration of a calibrator and the final volume comprises a known volumetric ratio of test sample to calibrating sample, wherein the calibrator comprises albumin coupled to a signal producing molecule;
depositing a loading fraction in a receiving well of an electrophoretic gel, wherein the loading fraction is a fraction of said final volume;

separating the loading fraction along a common separation lane of the electrophoretic gel such that components of the test sample and the calibrator are separated from one another along the common separation lane;

detecting the calibrator and separated components of test sample within the common separation lane; and measuring the level of the calibrator and separated components of the test sample based on said detecting, thereby performing electrophoresis with in-situ calibration.

* * * * *